US011744852B2

(12) United States Patent
Levy

(10) Patent No.: US 11,744,852 B2
(45) Date of Patent: Sep. 5, 2023

(54) HYDROGEN-CONTAINING COMPOSITION

(71) Applicant: HYEDGE IP COMPANY, Bryn Mawr, PA (US)

(72) Inventor: Gail Levy, Bryn Mawr, PA (US)

(73) Assignee: HYEDGE IP COMPANY, Bryn Mawr, PA (US)

( * ) Notice: Subject to any disclaimer, the term of this patent is extended or adjusted under 35 U.S.C. 154(b) by 242 days.

(21) Appl. No.: 17/207,185

(22) Filed: Mar. 19, 2021

(65) Prior Publication Data

US 2021/0205353 A1 Jul. 8, 2021

Related U.S. Application Data

(62) Division of application No. 15/310,595, filed as application No. PCT/US2015/030399 on May 12, 2015, now Pat. No. 10,953,041.

(60) Provisional application No. 62/116,339, filed on Feb. 13, 2015, provisional application No. 61/992,049, filed on May 12, 2014, provisional application No. 61/992,043, filed on May 12, 2014.

(51) Int. Cl.
| | |
|---|---|
| A61K 33/00 | (2006.01) |
| A23L 2/52 | (2006.01) |
| A23L 2/54 | (2006.01) |
| A61K 8/19 | (2006.01) |
| A61Q 17/04 | (2006.01) |
| A61Q 19/08 | (2006.01) |
| A61K 31/19 | (2006.01) |
| A61K 31/353 | (2006.01) |
| A61K 33/10 | (2006.01) |
| A61K 31/198 | (2006.01) |
| A61K 31/375 | (2006.01) |
| A61Q 19/00 | (2006.01) |
| A23L 2/44 | (2006.01) |
| A23L 2/02 | (2006.01) |
| A61K 9/00 | (2006.01) |
| A61K 36/00 | (2006.01) |

(52) U.S. Cl.
CPC .............. *A61K 33/00* (2013.01); *A23L 2/02* (2013.01); *A23L 2/44* (2013.01); *A23L 2/52* (2013.01); *A23L 2/54* (2013.01); *A61K 8/19* (2013.01); *A61K 9/0095* (2013.01); *A61K 31/19* (2013.01); *A61K 31/198* (2013.01); *A61K 31/353* (2013.01); *A61K 31/375* (2013.01); *A61K 33/10* (2013.01); *A61Q 17/04* (2013.01); *A61Q 19/00* (2013.01); *A61Q 19/08* (2013.01); *A23V 2002/00* (2013.01); *A61K 36/00* (2013.01); *A61K 2800/522* (2013.01); *A61K 2800/74* (2013.01)

(58) Field of Classification Search
None
See application file for complete search history.

(56) References Cited

U.S. PATENT DOCUMENTS

| | | |
|---|---|---|
| 8,562,860 B2 | 10/2013 | Sumita |
| 2002/0096792 A1 | 7/2002 | Valela |
| 2006/0112831 A1 | 6/2006 | Greenwald |
| 2009/0261486 A1 | 10/2009 | Olivier |
| 2010/0219260 A1 | 9/2010 | Matsuoka |
| 2012/0070540 A1 | 3/2012 | Igarashi |
| 2013/0066048 A1 | 3/2013 | Raskin |
| 2013/0108515 A1 | 5/2013 | Satoh |
| 2014/0010483 A1 | 1/2014 | Shih et al. |

FOREIGN PATENT DOCUMENTS

| | | |
|---|---|---|
| CN | 101484391 A | 7/2009 |
| CN | 102438954 A | 5/2012 |
| KR | 1020040056495 B1 | 7/2004 |
| KR | 100529006 B1 | 11/2005 |
| KR | 101244629 B1 | 3/2013 |

OTHER PUBLICATIONS

European Search Report dated Oct. 23, 2017.
Shigeo Ohta (2012) Biochimica Biophysica Acta 1820, Molecular hydrogen is a novel antioxidant to efficiently reduce oxidative stress with potential for the improvement of mitochondrial diseases, pp. 586-594.
Kawai, et al. (2012) Hepatology, Journal of the America Association for the study of liver diseases, vol. 56, No. 3, 10 pages.
International Search Report and Written Opinion.

*Primary Examiner* — Robert A Wax
*Assistant Examiner* — Randeep Singh
(74) *Attorney, Agent, or Firm* — Tarter Krinsky & Drogin LLP

(57) ABSTRACT

A hydrogen-containing composition for ingestion or topical use and method of producing the hydrogen-containing composition are provided. The composition includes a carrier liquid and molecular hydrogen. The concentration of molecular hydrogen in the carrier liquid is greater than 3 ppm.

10 Claims, 2 Drawing Sheets

HYDROGEN-CONTAINING COMPOSITION

CROSS REFERENCE TO RELATED APPLICATIONS

The benefit of priority under 35 U.S.C. § 120 of U.S. Provisional Patent Application No. 61/992,043 filed on May 12, 2014; U.S. Provisional Patent Application No. 61/992,049 filed on May 12, 2014; and U.S. Provisional Patent Application No. 62/116,339 filed on Feb. 13, 2015 are claimed, the disclosures of each of which are incorporated herein by reference in their entireties.

TECHNICAL FIELD

This disclosure is directed to a hydrogen-containing composition and a method for making the same.

BACKGROUND

Recently, antioxidants received a lot of attention because of the reported health benefits achieved by ingesting and topically applying anti-oxidants to skin. Many food, beverage, and skin care products in the marketplace have been extolled for their antioxidant properties.

Hydrogen is a strong antioxidant. Compositions, such as water containing hydrogen at the low ppm level, have been introduced. However, it has not been possible to increase the amount of hydrogen in water and beverage compositions to greater than 3.0 ppm. In addition, because hydrogen is a volatile gas, it rapidly evaporates from the hydrogen-containing compositions.

Oxidation in the body is natural for normal cellular function. Normal cell functions produce a small percentage of free radicals, but those free radicals are generally not a big problem. They are kept under control by antioxidants that a healthy body produces naturally.

What are problematic are external toxins, second hand cigarette smoke and air pollution. The latter are free radical generators. Food and water also harbor free radicals in the form of pesticides and other food additive toxins. Stress, lack of sleep, and excessive exercise all generate free radicals.

The saying that food is the best medicine no longer holds true. Humans used to receive many different and effective antioxidants in fruits, vegetables, whole grains, nuts, and legumes. Over the years these antioxidants or phytonutrients have been reduced by the food industry as a byproduct of making food taste better, have a greater shelf life, and better physical appearance. While agricultural land is diminishing, farmers are pressured to generate fruits and vegetables with less phytonutrients A consumer in the USA who wanted to easily purchase packaged water that gives some additional health benefits can purchase natural spring water or synthetically derived spring water (ionized water). The latter has not had any medical evaluation to confirm significant health benefits. A hydrogen stick that contains magnesium which gives off dilute hydrogen gas, but leaves magnesium and calcium byproducts in the water could also be used.

Some commercially available water from Asian countries contain low amounts of hydrogen, however, the water loses significant hydrogen because of the way it is packaged to the consumer.

Compositions for ingestion or topical use containing hydrogen in an increased concentration, and in which the hydrogen is held in the composition for a longer period of time, thereby providing a longer shelf life, is needed. A method for producing compositions with increased concentrations of hydrogen is needed.

SUMMARY

The present disclosure discloses a hydrogen-containing composition comprising a carrier liquid and molecular hydrogen. The concentration of molecular hydrogen in the carrier liquid is greater than 3 ppm.

In certain embodiments of the disclosure, the concentration of hydrogen in the carrier liquid is greater than 3 ppm to about 10 ppm. In other embodiments, the concentration of hydrogen in the carrier liquid ranges from 3.5 ppm to 6 ppm. In some embodiments, the concentration of hydrogen in the carrier liquid ranges from 4 ppm to 5.5 ppm.

The carrier liquid further comprises an oxygen scavenger in some embodiments. The oxygen scavenger comprises at least one selected from the group consisting of citric acid, ascorbic acid, sodium bicarbonate, calcium ascorbate, sodium ascorbate, a cranberry supplement, ginger, green tea, ethylenediaminetetraacetic acid, and combinations thereof.

In some embodiments of the disclosure, the composition is a beverage. When the liquid is a beverage, the liquid may be selected from the group consisting of water, juices, alcoholic beverages, soy-based beverages, soft drinks, energy drinks, coffee, tea, and dairy beverages, in certain embodiments. The juices include fruit and/or vegetable juices.

Some embodiments of the present disclosure further comprise a proanthocyanidin.

In certain embodiments, the carrier liquid is selected from the group consisting of water, juices, alcohols, soy-based beverages, soft drinks, energy drinks, coffee, tea, dairy beverages, oils, glycerol, dimethyl sulfoxide, and combinations thereof. The carrier liquid may be selected from the group consisting of alcoholic beverages, methanol, ethanol, isopropanol, vegetable oil, canola oil, sunflower oil, peanut oil, olive oil, palm oil, fish oil, coconut oil, sesame oil, castor oil, almond oil, mineral oil, and combinations thereof.

In certain embodiments of the present disclosure, the hydrogen-containing composition is a skin care composition. The skin care composition is a medicament in some embodiments and a cosmetic preparation in other embodiments. In certain embodiments, the skin care composition is a solution, a liniment, a foam, a spray, or an aerosol. In certain embodiments, the skin care composition comprises a solid portion. In certain embodiments, the skin care composition is a lotion, a cream, a gel, a paste, a patch, a plaster, or an ointment.

In certain embodiments of the disclosure, the hydrogen-containing composition is a hair care product, a bath product, or a beauty product.

Another embodiment of the present disclosure is a hydrogen-containing skin care composition comprising a carrier liquid containing molecular hydrogen, and a solid portion. The concentration of molecular hydrogen in the carrier liquid is greater than 0.1 ppm. The skin care composition can be a medicament or a cosmetic preparation.

In certain embodiments of the skin care composition, the concentration of hydrogen in the carrier liquid is greater than 0.1 ppm to about 10 ppm. The concentration of hydrogen in the carrier liquid is greater than 1 ppm to about 7 ppm in some embodiments. In certain embodiments, the concentration of hydrogen in the carrier liquid is greater than 2 ppm to about 6 ppm and the concentration of hydrogen in the carrier liquid is greater than 3 ppm to about 5 ppm in other embodiments.

The hydrogen-containing skin care composition is a lotion, a cream, a gel, a paste, a patch, a plaster, or an ointment in some embodiments.

The carrier liquid is selected from the group consisting of water, alcohols, oils, glycerol, dimethyl sulfoxide, and combinations thereof in certain embodiments of the hydrogen-containing skin care composition. The carrier liquid may be selected from the group consisting of methanol, ethanol, isopropanol, vegetable oil, canola oil, sunflower oil, peanut oil, olive oil, palm oil, fish oil, coconut oil, sesame oil, castor oil, almond oil, mineral oil, and combinations thereof.

The solid portion of the hydrogen-containing skin care composition is selected from the group consisting of a clay, talc, mica, silica, titania, magnesia, alumina, zinc oxide, calcium oxide, iron oxides, magnesium sulfate, and combinations thereof in certain embodiments.

The hydrogen-containing skin care composition may further comprise one or more of emulsifiers and thickening agents. In certain embodiments, the skin care composition further comprises one or more of a wax, paraffin, shea butter, lanolin, petroleum jelly, capsaicin, benzoin resin, and methyl salicylate. The skin care composition may further comprise a proanthocyanidin.

Another embodiment of the present disclosure is a method of producing a hydrogen-containing composition, comprising degassing a liquid, agitating the liquid, and chilling the liquid. Hydrogen gas at a pressure greater than atmospheric pressure is introduced into the liquid. The concentration of molecular hydrogen in the liquid is greater than 3 ppm.

In some embodiments of the disclosure, agitating the liquid includes mixing the liquid or vibrating the liquid. In some embodiments, the degassing and agitating the liquid are performed simultaneously. In certain embodiments, the degassing and chilling the liquid are performed simultaneously. The agitating and chilling the liquid are performed simultaneously in some embodiments, and the degassing, agitating, and chilling are performed simultaneously in certain embodiments.

The liquid is chilled to a temperature of greater than 0° C. to about 20° C. in certain embodiments.

In some embodiments, the hydrogen gas at a pressure greater than atmospheric pressure is bubbled into the liquid. The hydrogen gas is bubbled into the liquid by simultaneously passing the hydrogen gas and the liquid through one or more filters in certain embodiments.

DETAILED DESCRIPTION

The present disclosure discloses a hydrogen-containing composition comprising a carrier liquid and molecular hydrogen. The concentration of molecular hydrogen in the carrier liquid is greater than 3 ppm.

Figure 1:
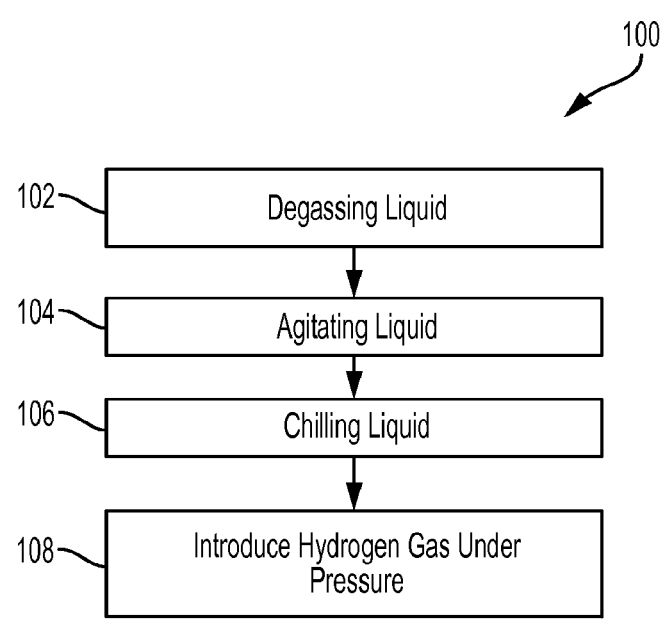
FIG. 1 is an exemplary process flow chart for producing a hydrogen-containing composition according to an embodiment of the present disclosure.

According to an embodiment of the disclosure, a method 100 of producing a hydrogen-containing composition includes the steps as set forth herein. As shown in FIG. 1, a method of producing a hydrogen-containing composition comprises a step 102 of degassing a liquid, a step 104 of agitating the liquid, and a step 106 of chilling the liquid. Hydrogen gas at a pressure greater than atmospheric pressure is introduced into the liquid in step 108.

In some embodiments of the disclosure, agitating the liquid includes mixing the liquid or vibrating the liquid. In some embodiments, the degassing and agitating the liquid are performed simultaneously. In certain embodiments, the degassing and chilling the liquid are performed simultaneously. The agitating and chilling the liquid are performed simultaneously in some embodiments, and the degassing, agitating, and chilling are performed simultaneously in certain embodiments.

In some embodiments, the hydrogen gas at a pressure greater than atmospheric pressure is bubbled into the liquid. The hydrogen gas is bubbled into the liquid by simultaneously passing the hydrogen gas and the liquid through one or more filters in certain embodiments.

Figure 2:
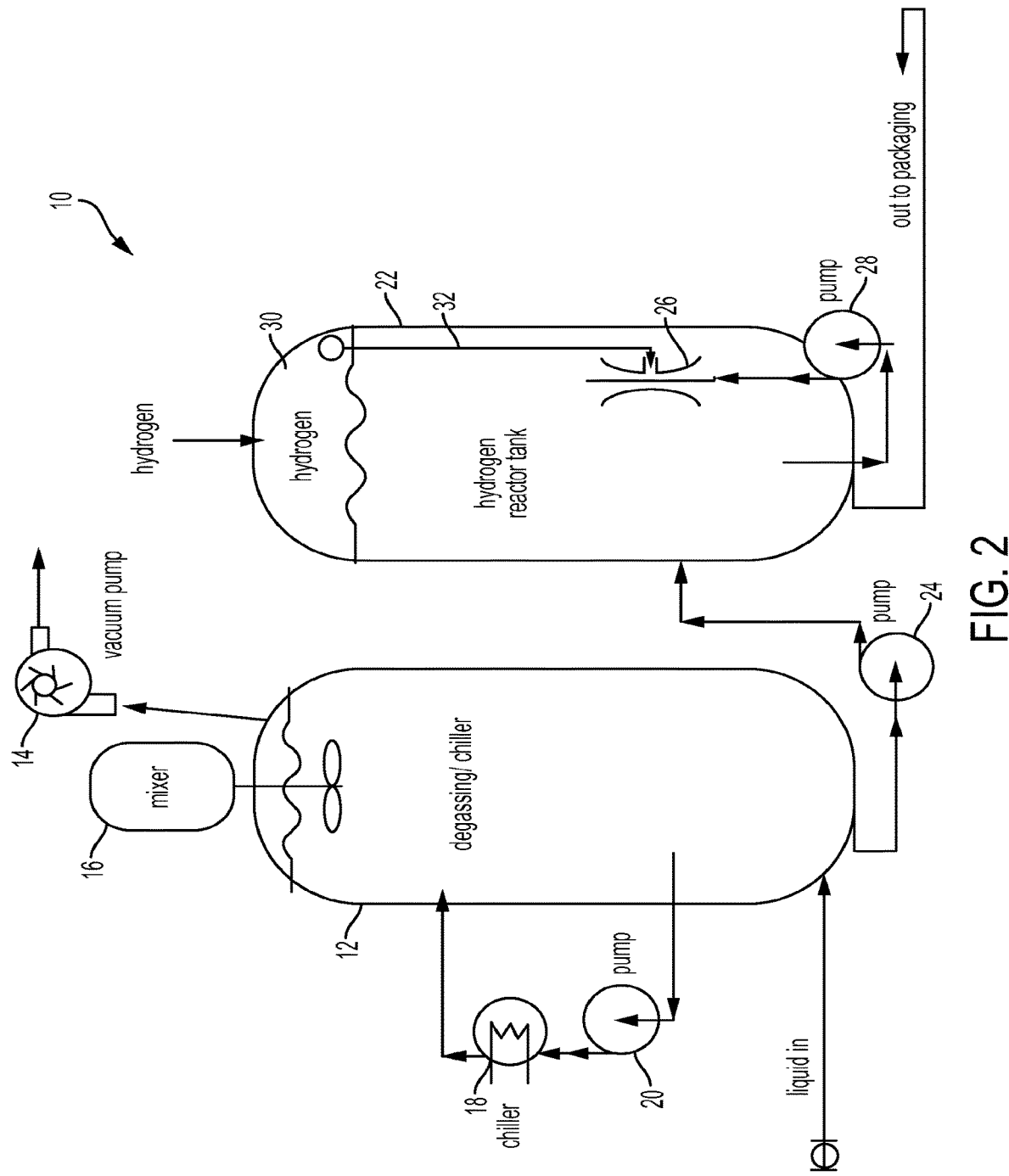
FIG. 2 shows an apparatus for producing a hydrogen-containing composition according to an embodiment of the present disclosure.

FIG. 2 shows an apparatus 10 for producing a hydrogen-containing composition according to an embodiment of the present disclosure. As shown in FIG. 2, a liquid, such as water, is pumped into a stainless steel vacuum process tank 12 to be degassed. Degassing is accomplished by pulling a vacuum on the liquid using a vacuum pump 14 to extract the entrained gasses from the liquid. In certain embodiments, the pressure in the process tank 12 is reduced to 380 torr or less. During the degassing period, the liquid will be agitated in certain embodiments. The agitation may be by a mechanical mixer 16. In other embodiments, the liquid is agitated by vibration. In some embodiments, the agitation may be produced by ultrasonic vibrations.

In some embodiments, as the liquid is being degassed, the temperature of the liquid is reduced, such as with a standard refrigerant chiller 18 by pumping the liquid through a liquid/liquid heat exchanger in the chiller 18 using a pump 20. The liquid is chilled to a temperature of greater than 0° C. to about 20° C. in certain embodiments. In certain embodiments, the target temperature for the liquid is about 1° C.

As used in this disclosure, the term "about" includes a range of 5% on either side of the recited value.

After the liquid is chilled, it is pumped into a stainless steel pressure rated process tank 22 using a pump 24 in certain embodiments. The pressure rated process tank 22 contains hydrogen gas. As the liquid level increases the pressure in the tank 22 will also increase. Inside the tank 22, the liquid is pumped through an eductor tube 26 using a pump 28. Pumping the water through the eductor tube 26 creates a low pressure in the tube 26. Inside the eductor tube 26 is an array of filters that intimately mix the hydrogen through the liquid. In certain embodiments, the filters are 10 micron sintered stainless steel filters. The fine 10 micron porous, sintered, stainless steel filters create a large number of very small bubbles of hydrogen in certain embodiments. The large number of bubbles creates extensive surface area for the transfer of hydrogen to the water being pumped past the bubbles.

The hydrogen to supply the bubbles comes from the top of the tank "head space" 30 that is filled with compressed hydrogen. In certain embodiments, 99.999% pure $H_2$ gas available from Linde is used as the hydrogen source. The hydrogen is drawn into the filters through a tube 32 from the top of the head space down to the eductor tube 26 filter array. An optional meter installed in the side of the tank 22 can measure the concentration of hydrogen in the liquid, thereby ensuring the proper concentration of concentration in the liquid. When the desired hydrogen concentration is obtained, the hydrogen-containing liquid is dispensed from the tank 22 into suitable packaging.

Production demands will dictate the size and quantity of the tanks required to process the water. In certain embodiments, at least 3 vacuum degassing tanks are used to meet production needs. For example, at a given point in the process:

one tank is filling with incoming water;
a second tank is chilling and degassing the water; and
a third tank is feeding the water to the process tanks containing hydrogen.

Each tank will all perform all 3 steps in certain embodiments. The three tanks may be synchronized and switching between tanks can be accomplished automatically using actuators. The process order for the 3 vacuum degassing tanks may be as set forth below.

Tank 1—fill/chill, degas/feed
Tank 2—chill, degas/feed/fill
Tank 3—feed/fill/chill, degas.

The chilled degassed water is subsequently fed to 3 process tanks in a certain embodiment. For example, at a given point in the process:

the degassed chilled water fills the first tank;
the hydrogen is percolated with the water in the second tank; and
the third tank provides water for the packaging line.

All of the 3 process tanks can feed the packaging line. Just as with the degassing process, the tanks may each be on a different process step and can be switched automatically with actuators. The process order for the 3 process tanks may be as set forth below:

Tank 1—fill/hydrogen percolation/packaging supply
Tank 2—hydrogen percolation/packaging supply/fill
Tank 3—packaging supply/fill/hydrogen percolation.

The packaging fill rate depends on how long it takes to reach the desired concentration of hydrogen in the water.

In hydrogen-containing compositions according to the present disclosure, the concentration of hydrogen in the carrier liquid is greater than 3 ppm to about 10 ppm. In other embodiments, the concentration of hydrogen in the carrier liquid ranges from 3.5 ppm to 6 ppm. In some embodiments, the concentration of hydrogen in the carrier liquid ranges from 4 ppm to 5.5 ppm.

The carrier liquid may be any liquid suitable for ingestion or topical application. Suitable carrier liquids include water; beverages, including juices, alcoholic beverages, soy-based beverages, soft drinks, energy drinks, coffee and tea, including iced coffee and iced tea, and daily beverages; oils, including vegetable oil, canola oil, sunflower oil, peanut oil, olive oil, palm oil, fish oil, coconut oil, sesame oil, castor oil, almond oil, and mineral oil; glycerol; dimethyl sulfoxide; alcohols, including methanol, ethanol, and isopropanol; and combinations thereof.

In some embodiments, the amount of oxygen is reduced in the liquid by adding a scavenger to the liquid, which reacts with oxygen, such as ascorbic acid. The use of ascorbic acid is further beneficial because ascorbic acid has medicinal value.

In other embodiments of the disclosure, the oxygen scavenger comprises at least one selected from the group consisting of citric acid, ascorbic acid, sodium bicarbonate, calcium ascorbate, sodium ascorbate, a cranberry supplement, ginger, green tea, ethylenediaminetetraacetic acid (EDTA), and combinations thereof.

In certain embodiments, the liquid or beverage may comprise a proanthocyanidin to provide increased concentration of hydrogen in the liquid. The proanthocyanidin may be directly added to the liquid, or a component with a sufficiently high concentration of proanthocyanidin may be added to the liquid. The component may be, for example, a fruit, vegetable, cereal, or nut containing proanthocyanidins, or a juice or extract thereof.

Sources of proanthocyanidins which may be used in embodiments of the liquid include: blueberries, including cultivated highbush blueberries and lowbush blueberries; cranberries; blackberries; marion berries; choke berries; raspberries; strawberries; blackcurrants; cherries; grapes, including green grapes and red grapes; dry grape seed; apples, including red delicious, with and without peel, golden delicious, with and without peel, granny smith, gala, fuji, and apple sauce; peaches, including canned peaches in heavy syrup; pears, including green cultivars; nectarines; plums, including black and black diamond; apricots; kiwis, including gold kiwis; avocados; mangos; dates, including fresh deglet noor dates; bananas; raw indian squash; sorghum, including sumac bran, sumac whole grain, hi-tannin whole grain, hi-tannin whole grain extrudate; pinto beans, including raw and simmered; small red beans; red kidney beans; barley; black eyed peas; black beans; hazelnuts; pecans; pistachios; almonds; walnuts; roasted peanuts; peanut butter; cashews; chocolate, including baking, unsweetened, black, and milk chocolate; chocolate milk; red wine; beer; cranberry juice cocktail; grape juice; apple juice; ground cinnamon; curry powder; turmeric; and combinations thereof. In certain embodiments, the source of proanthocyanidins may be cranberry juice, plums, or other high-concentration sources of proanthocyanidin.

When the liquid according to the present disclosure is to be ingested, such as water, the water is first filtered, or undergoes reverse osmosis in some embodiments. Alternatively, the water can be subjected to ozonation or ultraviolet light treatment to sterilize the water.

In certain embodiments of the present disclosure, the hydrogen-containing composition is a skin care composition. The hydrogen-containing composition is a medicament in some embodiments and a cosmetic preparation in other embodiments. In certain embodiments, the skin care composition is a solution, a liniment, a foam, a spray, or an aerosol. In certain embodiments, the skin care composition comprises a solid portion. In certain embodiments, the skin care composition is a lotion, a cream, a gel, a paste, a patch, a plaster, or an ointment.

In certain embodiments of the disclosure, the hydrogen-containing composition is a hair care product, a bath product, or a beauty product.

In another embodiment of the present disclosure, a skin care composition containing molecular hydrogen is provided. The hydrogen-containing skin care composition comprises a carrier liquid containing molecular hydrogen, and a solid portion. The concentration of molecular hydrogen in the carrier liquid is greater than 0.1 ppm.

The skin care composition containing molecular hydrogen may prevent wrinkles and damage from exposure to UVA radiation. The skin care composition may also be used to treat eczema and psoriasis.

In certain embodiments of the skin care composition, the concentration of hydrogen in the carrier liquid is greater than 0.1 ppm to about 10 ppm. The concentration of hydrogen in the carrier liquid is greater than 1 ppm to about 7 ppm in some embodiments. In certain embodiments, the concentration of hydrogen in the carrier liquid is greater than 2 ppm to about 6 ppm and the concentration of hydrogen in the carrier liquid is greater than 3 ppm to about 5 ppm in other embodiments.

The skin care composition is a medicament in some embodiments and a cosmetic preparation in other embodiments. In certain embodiments, the skin care composition is a solution, a liniment, a foam, a spray, or an aerosol. In certain embodiments, the skin care composition comprises a solid portion. In certain embodiments, the skin care composition is a lotion, a cream, a gel, a paste, a patch, a plaster, or an ointment.

In certain embodiments, the solid portion of the composition includes one or more selected from a clay, including kaolinite, attapulgite, montmorillonite-smectite, illite, sepiolite, and palygorskite; talc; mica; silica; titania; magnesia; alumina; zinc oxide; calcium oxide; iron oxides; and magnesium sulfate.

In certain embodiments, the skin care composition includes one or more of emulsifiers and thickening agents.

In some embodiments, the skin care composition includes one or more of a wax, including beeswax and carnauba wax; paraffin; shea butter; lanolin; petroleum jelly; capsaicin; benzoin resin; and methyl salicylate.

In another embodiment of the present disclosure, a hair care product, a bath product, and a beauty product containing molecular hydrogen is provided. The hydrogen-containing skin care composition comprises a carrier liquid containing molecular hydrogen, and a solid portion. The concentration of molecular hydrogen in the carrier liquid is greater than 0.1 ppm.

In certain embodiments of the hair care products, and bath and beauty products, the concentration of hydrogen in the carrier liquid is greater than 0.1 ppm to about 10 ppm. The concentration of hydrogen in the carrier liquid is greater than 1 ppm to about 7 ppm in some embodiments. In certain embodiments, the concentration of hydrogen in the carrier liquid is greater than 2 ppm to about 6 ppm and the concentration of hydrogen in the carrier liquid is greater than 3 ppm to about 5 ppm in other embodiments.

In addition, other ingredients commonly found in skin care compositions, hair care products, and bath and beauty products can be included in embodiments of the present disclosure.

The inventor has found that the hydrogen-containing composition described in the present disclosure has an unexpectedly increased concentration of molecular hydrogen in the carrier liquid than in previously disclosed hydrogen-containing liquids and beverages.

The inventor has found that the methods of the present disclosure produce a carrier liquid having an unexpectedly increased concentration of molecular hydrogen in the liquid and beverage than in previously disclosed liquids and beverages.

The inventor has found that a concentration of greater than 3 ppm of molecular hydrogen in a carrier liquid or beverage is an unexpected improvement over previously disclosed liquids and beverages.

The inventor has found that a concentration of greater 0.1 ppm molecular hydrogen in the carrier liquid of skin care composition, hair care product, and bath and beauty products is unexpected over previously disclosed skin care compositions.

The embodiments illustrated in the instant disclosure are for illustrative purposes only. They should not be construed to limit the claims. As is clear to one of ordinary skill in the art, the instant disclosure encompasses a wide variety of embodiments not specifically illustrated herein. While the compositions and methods of this disclosure have been described in terms of exemplary embodiments, it will be apparent to those of skill in the art that variations may be applied to the compositions and methods and in the steps or in the sequence of steps of the method described herein without departing from the concept, spirit and scope of the invention.

The invention claimed is:

1. An apparatus for producing a hydrogen-containing composition comprising:
    at least one process tank for receiving a carrier liquid;
    a first pump for creating a vacuum on the carrier liquid thereby extracting gasses from the carrier liquid;
    a mixer for agitating the carrier liquid;
        a second pump for directing the carrier liquid into a chiller, the chiller reducing a temperature of the carrier liquid within a range of 0° C. to 20° C.;
    a third pump for pumping the chilled, agitated, degassed carrier liquid into a hydrogen reactor tank, the hydrogen reactor tank containing hydrogen gas, wherein the third pump causes the hydrogen reactor tank to become pressurized by compressing the hydrogen gas in a head space of the hydrogen reactor tank; and
    a fourth pump for drawing the compressed hydrogen gas from the head space of the hydrogen reactor tank into an eductor tube and pumping the carrier liquid through the eductor tube located within the hydrogen reactor tank, the eductor tube being an array of filters that mixes the compressed hydrogen gas with the carrier liquid by transferring the hydrogen gas to the carrier liquid through bubbles created by the eductor tube,
    wherein a concentration of the hydrogen gas in the carrier liquid within the hydrogen reactor tank is in a range of 3 ppm to 10 ppm.

2. The apparatus of claim 1 wherein the liquid is water.

3. The apparatus of claim 1 wherein the at least one process tank is a stainless-steel vacuum process tank.

4. The apparatus of claim 1 wherein the mixer is a mechanical mixer.

5. The apparatus of claim 1 wherein the mixer is a vibrational mixer.

6. The apparatus of claim 5 wherein the vibrational mixer produces ultrasonic vibrations.

7. The apparatus of claim 1 wherein the chiller is a liquid/liquid heat exchanger.

8. The apparatus of claim 1 wherein the array of filters are micron-sintered, stainless-steel filters.

9. The apparatus of claim 1 wherein the hydrogen gas is drawn into the array of through a tube.

10. The apparatus of claim 1 further comprising:
    a meter for measuring concentration of the hydrogen gas in the carrier liquid within the hydrogen reactor tank.

* * * * *